(12) United States Patent
Donde et al.

(10) Patent No.: US 7,101,904 B2
(45) Date of Patent: Sep. 5, 2006

(54) CYCLOPENTANE HEPTAN(ENE)OIC ACID, 2-HETEROARYLALKENYL DERIVATIVES AS THERAPEUTIC AGENTS

(75) Inventors: Yariv Donde, Dana Point, CA (US); Robert M. Burk, Laguna Beach, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 93 days.

(21) Appl. No.: 10/915,987

(22) Filed: Aug. 10, 2004

(65) Prior Publication Data

US 2006/0035961 A1     Feb. 16, 2006

(51) Int. Cl.
C07D 333/10 (2006.01)
A61K 31/381 (2006.01)
C07D 333/28 (2006.01)
C07D 333/32 (2006.01)

(52) U.S. Cl. ............... 514/438; 514/445; 549/62; 549/78

(58) Field of Classification Search .................. None
See application file for complete search history.

(56) References Cited

U.S. PATENT DOCUMENTS

| | | | |
|---|---|---|---|
| 4,119,727 A | 10/1978 | Buendia et al. | 424/275 |
| 4,166,452 A | 9/1979 | Generales et al. | 128/741 |
| 4,256,108 A | 3/1981 | Theeuwes | 128/260 |
| 4,265,874 A | 5/1981 | Bonsen et al. | 424/15 |
| 4,994,274 A | 2/1991 | Chan et al. | 424/427 |
| 5,028,624 A | 7/1991 | Chan et al. | 514/530 |
| 5,034,413 A | 7/1991 | Chan et al. | 514/530 |
| 5,385,945 A | 1/1995 | Garst et al. | 514/613 |
| 5,446,041 A | 8/1995 | Chan et al. | 514/530 |
| 5,599,838 A * | 2/1997 | Sato et al. | 514/530 |
| 5,688,819 A | 11/1997 | Woodward et al. | 514/357 |
| 5,741,810 A * | 4/1998 | Burk | 514/438 |
| 5,834,498 A | 11/1998 | Burk | 514/445 |
| 5,972,991 A * | 10/1999 | Burk | 514/438 |
| 6,124,344 A * | 9/2000 | Burk | 514/438 |
| 6,248,773 B1 * | 6/2001 | Burk | 514/438 |
| 6,376,533 B1 * | 4/2002 | Burk et al. | 514/438 |
| 6,586,462 B1 * | 7/2003 | Burk et al. | 514/438 |
| 6,680,337 B1 * | 1/2004 | Burk | 514/438 |
| 2002/0094981 A1 * | 7/2002 | Ponticello et al. | 514/226.8 |

FOREIGN PATENT DOCUMENTS

| | | |
|---|---|---|
| WO | WO 99/25358 | 5/1999 |
| WO | WO 02/100388 | 12/2002 |
| WO | WO 03/002755 | 1/2003 |

OTHER PUBLICATIONS

Bito, L.Z. *Biological Protection with Prostaglandins*, Cohen, M.M., ed., Boca Raton, Fla, CRC Press Inc., 1985, pp. 231-252.
Bito, L.Z., *Applied Pharmacology in the Medical Treatment of Glaucomas* Drance, S.M. and Neufeld, A.H. eds., New York, Grune & Stratton, 1984, pp. 477-505.
Bito, L.Z., *Arch. Ophthalmol. 105,* 1036 (1987).
Francis A. Carey, Organic Chemistry, New York: McGraw-Hill Book Company 1987, p. 63.
Nilsson et. al., *Invest. Ophthalmol. Vis. Sci.* (suppl), 284 (1987).
Remington's Pharmaceutical Sciences, Mack Publishing Company, Easton, Pa., 16th Edition, 1980.
Siebold et al., *Esterified Prostaglandin Shows 'Potent' Promise*, Ocular Surgery News, vol. 1, No. 3 (Feb. 1989); pp. 3, 59.

* cited by examiner

*Primary Examiner*—Kamal A. Saeed
*Assistant Examiner*—Nyeemah Grazier
(74) *Attorney, Agent, or Firm*—Brent A. Johnson; Robert J. Baran; Martin A. Voet

(57) ABSTRACT

A compound

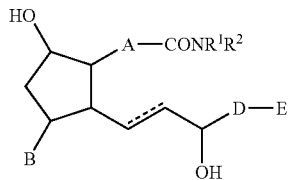

or a pharmaceutically acceptable salt or a prodrug thereof, wherein A, B, $R^1$, $R^2$, D, and E are defined herein. Use of the diseases for the treatment of diseases, and compositions and medicaments related thereto are also disclosed.

21 Claims, 2 Drawing Sheets

Figure 1:
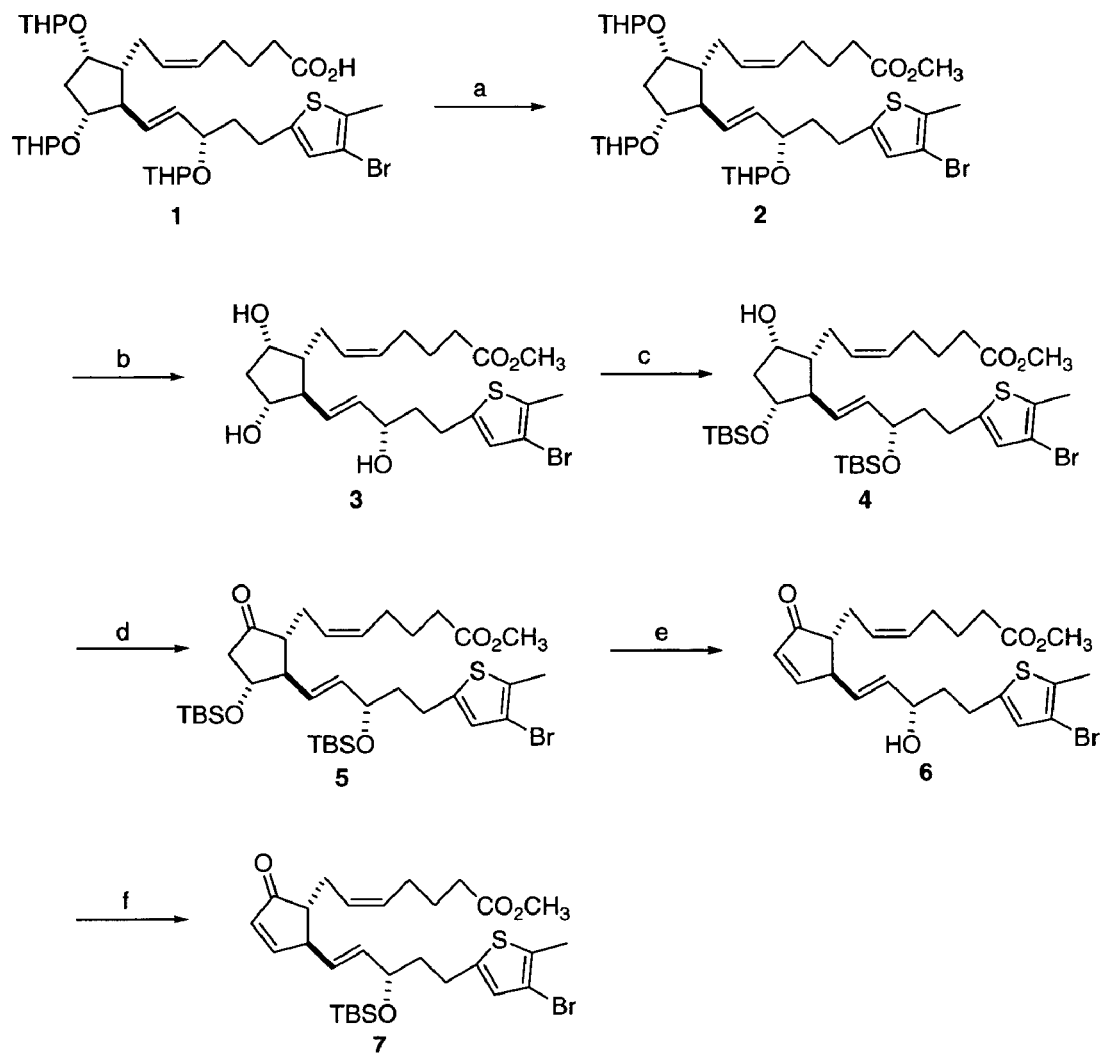

(a) MeI, DBU, acetone; (b) PPTs, MeOH; (c) TBSCl, Et₃N, DMAP, CH₂Cl₂; (d) TPAP, NMO, 4A MS CH₂Cl₂; (e) HOAc, THF, H₂O 70 °C; (f) TBSOTf, 2,6-lutidine, CH₂Cl₂.

(a) R$_2$CuM or [PhP$_3$CuH]$_6$; (b) NaBH$_4$, MeOH (ca. 1:1 diastereomers); (c) HOAc; THF, H$_2$O 70 °C; separate C9 diastereomers; (d) 0.5 M LiOH, THF; (e) ClCO$_2$Et, Et$_3$N, CH$_2$Cl$_2$;R'NH$_2$or NH$_4$OH (aq).

CYCLOPENTANE HEPTAN(ENE)OIC ACID, 2-HETEROARYLALKENYL DERIVATIVES AS THERAPEUTIC AGENTS

BACKGROUND OF THE INVENTION

Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

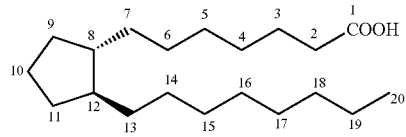

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et. al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of U.S. patents assigned to Allergan, Inc. prostaglandin esters with increased ocular hypotensive activity accompanied with no or substantially reduced side-effects are disclosed. Some representative examples are U.S. Pat. No. 5,446,041, U.S. Pat. No. 4,994,274, U.S. Pat. No. 5,028,624 and U.S. Pat. No. 5,034,413 all of which are hereby expressly incorporated by reference.

U.S. Pat. No. 5,688,819, commonly assigned to Allergan, Inc., and incorporated herein by reference discloses compounds known as prostamides. It has been shown that prostamides have pronounced effects on smooth muscle and are potent ocular hypotensive agents. Additionally, prostamides cause significantly lower ocular surface hyperemia than prostaglandins. One prostamide exemplary of the these effects is bimatoprost, which is marketed by Allergan, Inc. under the trade name Lumigan®, which has the structure shown below.

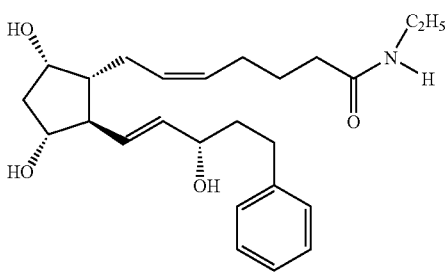

U.S. Pat. No. 5,385,945, commonly assigned to Allergan, Inc., discloses certain 11-dihydro derivatives of certain prostamides.

In citing the foregoing references, and other references cited herein, applications make no admission as to whether any of said references constitutes prior art.

BRIEF DESCRIPTION OF THE INVENTION

Disclosed herein are compounds comprising

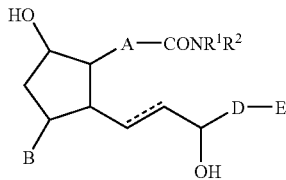

or a pharmaceutically acceptable salt or a prodrug thereof, wherein
a dashed line represents the presence or absence of a bond;
A is —(CH$_2$)$_6$—, or cis-CH$_2$—CH=CH—(CH$_2$)$_3$—, wherein 1 or 2 carbons may be substituted with S or O;
B is hydrogen, a C$_{1-6}$ hydrocarbon, —(CH$_2$)$_m$X(CH$_2$)$_p$H, wherein m is at least 1 and the sum of m and p is from 1 to 5;
R$^1$ and R$^2$ are independently H, C$_{1-6}$ alkyl, or C$_{1-6}$ hydroxyalkyl;
D is —(CH$_2$)$_n$—, —CH$_2$X(CH$_2$)$_n$—, or —(CH$_2$)$_n$X—, wherein n is from 0 to 4 and X is S or O; and
E is a moiety comprising a chain of from 2 to 12 non-hydrogen atoms.

Methods of treating certain diseases and methods of manufacturing medicaments comprising the compounds contemplated herein are also disclosed.

BRIEF DESCRIPTION OF THE DRAWING FIGURES

Figure 2:
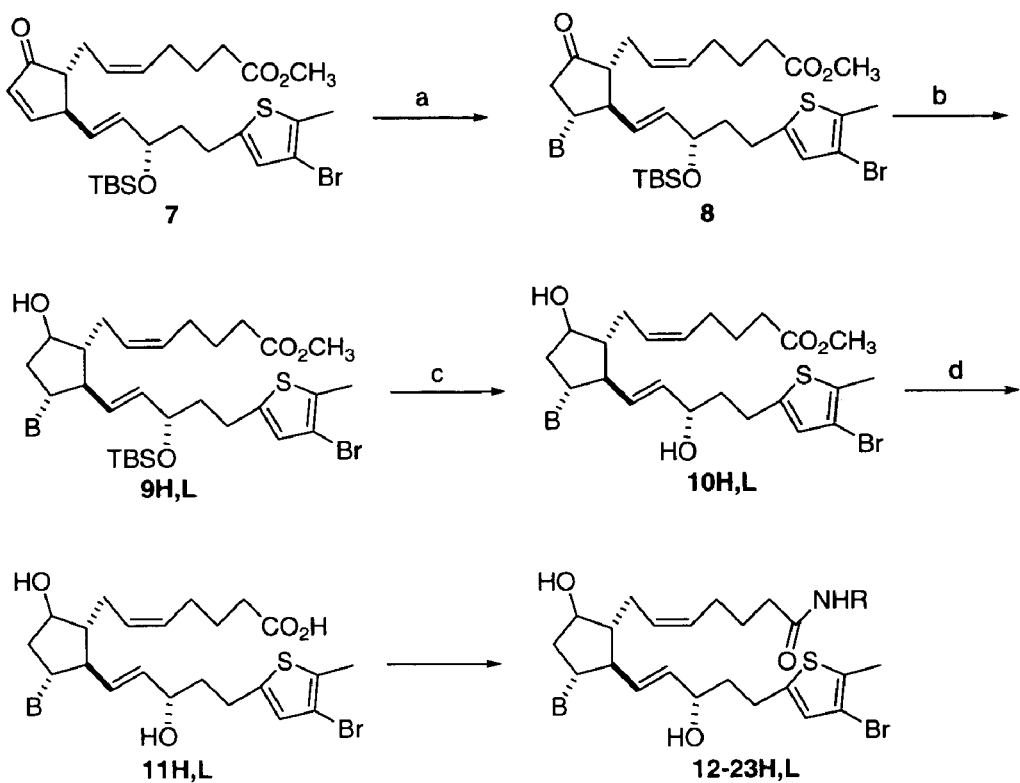

FIGS. 1 and 2 depict one method by which compounds disclosed herein may be prepared.

DETAILED DESCRIPTION OF THE INVENTION

Several of the carbon atoms on these compounds are chiral centers. While not intending to limit the scope of the invention in any way, or be bound in any way by theory, it is believed that many compounds and pharmaceutically active salts or prodrugs thereof having the stereochemistry shown below are particularly useful.

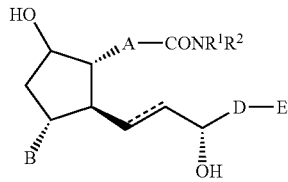

However, it is also advantageous if one or more of the bonds has the indicated stereochemistry, while the stereochemistry of other bonds to chiral centers may vary. Thus, while not intending to limit the scope of the invention in any way, compounds comprising

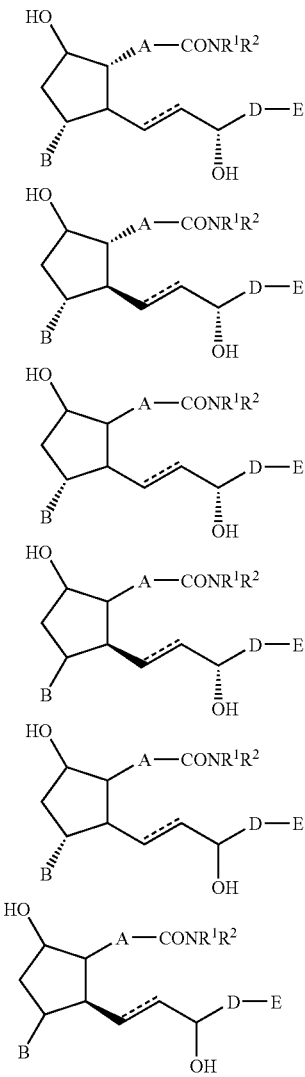

or the like and pharmaceutically acceptable salts and prodrugs thereof, are particularly useful in the context disclosed herein.

In relation to the identity of A disclosed in the chemical structures presented herein, in the broadest sense, A is —(CH$_2$)$_6$—, or cis-CH$_2$CH=CH—(CH$_2$)$_3$—, wherein 1 or 2 carbons may be substituted with S or O. In other words, A may be —(CH$_2$)$_6$—, cis-CH$_2$CH=CH—(CH$_2$)$_3$—, or A may be a group which is related to one of these two moieties in that any carbon is substituted with S or O. For example, while not intending to limit the scope of the invention in any way, A may be an S substituted moiety such as one of the following or the like.

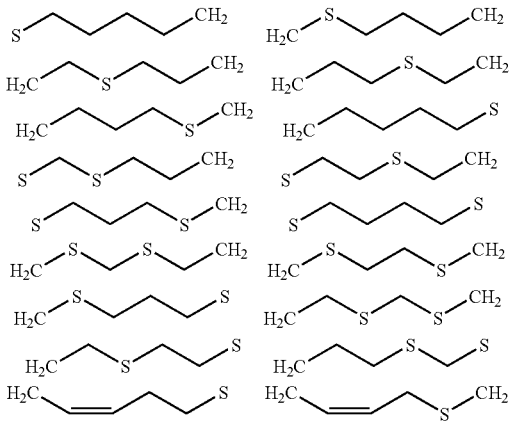

Alternatively, while not intending to limit the scope of the invention in any way, A may be an O substituted moiety such as one of the following or the like.

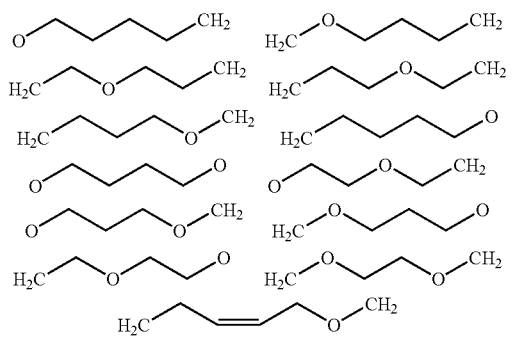

In other embodiments, A is —(CH$_2$)$_6$— or cis-CH$_2$CH=CH—(CH$_2$)$_3$— having no heteroatom substitution.

In relation to the identity of R$^1$ and R$^2$, and in other relevant places herein "C$_{1-6}$ alkyl" refers to an alkyl group, as generally understood in the art, having from 1 to 6 carbon atoms, whether it is linear, branched, or cyclic. Thus, a "C$_{1-6}$ alkyl" could be methyl; ethyl; n-propyl, or iso-propyl; a linear or branched n-butyl isomer; a linear or branched pentyl isomer; or a linear or branched hexyl isomer. Further, one or more cyclic structures could be included provided that no double bond is present. Thus, "C$_{1-6}$ alkyl" could be cyclopropyl, methylcyclopropyl, dimethylcyclopropyl, ethylcyclopropyl, propylcyclopropyl, etc.; methylcyclobutyl, dimethylcyclobutyl, etc.; methylpentyl; or cyclohexyl. "C$_{1-6}$ hydroxyalkyl" refers to a C$_{1-6}$ alkyl comprising a hydroxyl group, including, but not limited to, hydroxymethyl, hydroxyethyl, a propyl isomer with a hydroxyl group, a butyl isomer with a hydroxyl group, a pentyl isomer with a hydroxyl group, a hexyl isomer with a hydroxyl group, or a cycloalkyl having a hydroxyl group.

R$^1$ and R$^2$ may also be connected such that a ring is formed such as in the compound shown below.

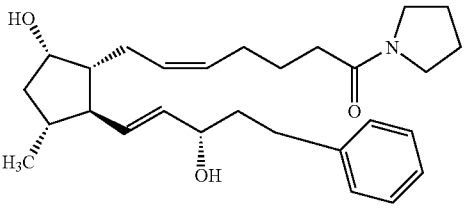

While not intending to limit the scope of the invention in any way, in some of the compounds R$^1$ is H, while R$^2$ is H, ethyl, or hydroxyethyl.

B is hydrogen, a C$_{1-6}$ hydrocarbon, or —(CH$_2$)$_m$X(CH$_2$)$_p$H, wherein m is at least 1 and the sum of m and p is from 1 to 5. A hydrocarbon is a moiety having only carbon and hydrogen such as a C$_{1-6}$ alkyl; a C$_{2-6}$ alkenyl; a C$_{2-6}$ alkynyl; phenyl; or the like. An alkenyl should be broadly understood to be an alkyl having one or more C=C bonds such as ethenyl, propenyl, butadienyl; cyclopentenyl; and the like. An alkynyl should be broadly understood to be an alkyl having one or more C≡C bonds such as ethynyl, propynyl; butadiynyl, and the like. Combinations of any of the above are also possible.

Alternatively, B may be —(CH$_2$)$_m$X(CH$_2$)$_p$H, wherein m is at least 1 and the sum of m and p is from 1 to 5. Thus, B may be an ethereal moiety having from 1 to 5 carbon atoms such as —CH$_2$OCH$_3$, —CH$_2$CH$_2$OCH$_3$, etc.; or a hydroxyalkyl having from one to five carbon atoms such as hydroxymethyl (—CH$_2$OH), hydroxyethyl, etc. Sulfur containing analogs are also possible, i.e. where X is S.

In relation to the identity of D, D is —(CH$_2$)$_n$—, —CH$_2$X(CH$_2$)$_n$—, or —(CH$_2$)$_n$X—, wherein n is from 0 to 4 and X is S or O. In other words, while not intending to be limiting, D may be a bond, —CH$_2$—, —CH$_2$CH$_2$—, —CH$_2$CH$_2$CH$_2$—, —(CH$_2$)$_4$—, —CH$_2$S—, —CH$_2$O—, —CH$_2$SCH$_2$—, —CH$_2$SCH$_2$CH$_2$—, —CH$_2$SCH$_2$CH$_2$CH$_2$—, —CH$_2$SCH$_2$CH$_2$CH$_2$—, —CH$_2$CH$_2$S—, —CH$_2$CH$_2$CH$_2$S—, —CH$_2$OCH$_2$—, —CH$_2$OCH$_2$CH$_2$—, —CH$_2$OCH$_2$CH$_2$CH$_2$—, —CH$_2$OCH$_2$CH$_2$CH$_2$CH$_2$—, —CH$_2$CH$_2$O—, —CH$_2$CH$_2$CH$_2$O—, and the like. A person of ordinary skill in the art will understand that n is required to be an integer.

Certain compounds comprise

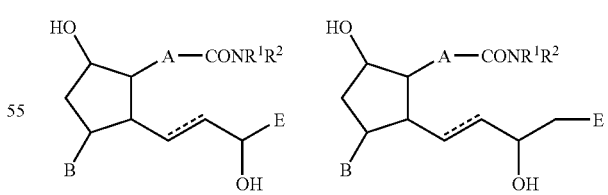

or a pharmaceutically acceptable salt or a prodrug thereof.

In relation to E, E is a moiety comprising a chain of from 2 to 12 non-hydrogen atoms. In this regard, a chain is the most direct connection from the point of attachment of the moiety to the most remote non-hydrogen atom. The most remote non-hydrogen atom is the atom which is connected to the point of attachment for E through the largest number of atoms by the most direct route. For example, the moiety below comprises a chain, shown in bold, of 12 non-hydrogen atoms.

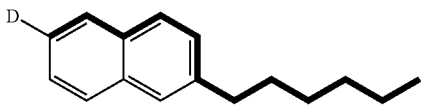

In the example below, the moiety comprises a chain of 4 non-hydrogen atoms.

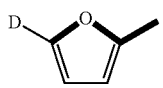

The moiety shown below comprises a chain of 6 non-hydrogen atoms.

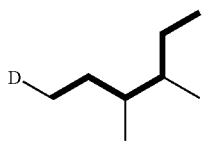

In certain compounds E is an aromatic or heteroaromatic moiety, or a substituted aromatic or heteroaromatic moiety having substituents comprising from 1 to 6 non-hydrogen atoms each. In other words, in these compounds E can be an aromatic moiety such as phenyl, napthyl, etc, or E can be a heteroaromatic moiety such as thienyl, pyridinyl, furyl, benzothienyl, etc. Alternatively, E can be one of these aromatic or heteroaromatic moieties, which is substituted with substituents comprising from 1 to 6 non-hydrogen atoms each. Thus, E may have one substituent, or it can have as many substituents as the ring will bear. For example, while not intending to limit the scope of the invention in any way E could be a substituted phenyl with from 1 to 5 substituents which may be the same or mixed such as a monosubstituted phenyl such as methylphenyl, chlorophenyl, etc.; a disubstituted phenyl having the same substituents such as dichlorophenyl, or mixed substituents such as ethylmethylphenyl, etc.; a trisubstituted phenyl; a tetrasubstituted phenyl; or a pentasubstituted phenyl.

Similarly, while not intending to be limiting, a napthyl moiety could have up to 7 substituents. Heteroaromatic moieties may also bear a number of subsituents although, while not intending to be limiting, some heteroaromatic moieties may not be able to bear a substituent on the heteroatom. For example, while not intending to be limiting, a furyl moiety having an O-substituent is unlikely to be stable.

Substituents having up to 6 non-hydrogen atoms may include, but are not limited to, hydrocarbons having up to six carbons such as methyl, ethyl, propyl isomers, butyl isomers pentyl isomers, hexyl isomers, etc., analogous unsaturated hydrocarbons including alkenyl, alkynyl, and cyclic hydrocarbons; alkoxy having up to 5 carbon atoms; halogens, including fluoro, chloro, and bromo; hydroxyl; trifluoromethyl; $CO_2H$; $CN$; $NO_2$; $SO_3H$; etc. Each substituent may have up to 6 non-hydrogen atoms.

These substituents may be in any reasonable position on the aromatic or heteroaromatic moiety. A person of ordinary skill in the art will understand that the number of substituents will be an integer.

In one embodiment E is an aromatic or heteroaromatic moiety having from 0 to 4 substituents selected from the group consisting of methyl, methoxy, —CN, bromo, chloro, fluoro, and trifluoromethyl. For example, while not intending to be limiting, E could be unsubstituted thienyl or another heteroaromatic or aromatic ring, or E could be a substituted aromatic or heteroaromatic moiety including a monosubstituted thienyl such as methylthienyl or bromothienyl; a disubstituted thienyl moiety having identical substituents such as dimethylthienyl or dibromothienyl, or mixed substituents such as bromomethylphenyl; a trisubstituted thienyl moiety having identical or mixed substituents; a tetrasubstituted thienyl having identical or mixed substituents; a mono-, di-, tri-, or tetra-substituted phenyl; or any other aromatic or heteroaromatic moiety having up to 4 substituents.

In other embodiments E is an aromatic or heteroaromatic moiety having from 1 to 3 substituents, wherein said aromatic moiety is selected from the group consisting of phenyl, thienyl, benzothienyl, and napthyl, and said substituents are selected from the group consisting of methyl, methoxy, bromo, chloro, and fluoro. These substituents may be in any reasonable position on the aromatic or heteroaromatic moiety.

In other embodiments, E is phenyl or thienyl having from 2 to 4 substituents. These substituents may be in any reasonable position on the phenyl or thienyl moiety.

While not intending to limit the scope of the invention in any way, in other embodiments, E is an aromatic or a heteroaromatic moiety consisting of a single aromatic ring and one or two substituents, said ring consisting of five or six atoms, and said substituents being selected from the group consisting of bromo, chloro, flouro, methyl, and methoxy. In other words, E is a single aromatic or heteroaromatic ring of five or six members (i.e. not a fused ring moiety such as naphthyl or benzothienyl) having one or two of the substituents listed. While not intending to be limiting, some possible examples such aromatic rings consisting of five or six atoms include phenyl, furyl, pyridinyl, thienyl, thiazolyl, pyrimidinyl, pyrrolyl, and imidazolyl.

A person of ordinary skill in the art will understand that the number of substituents on an aromatic ring will be an integer.

Compounds comprising

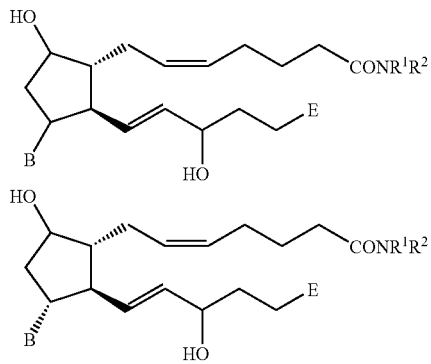

-continued

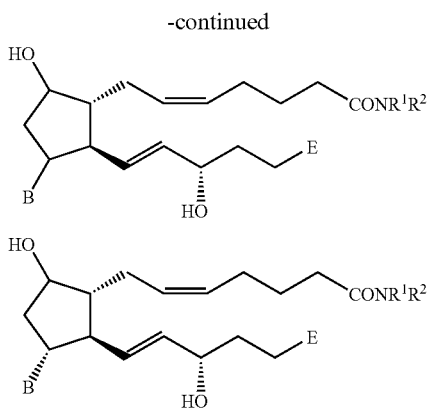

or a pharmaceutically acceptable salt or a prodrug thereof are also contemplated herein.

Another embodiment comprises

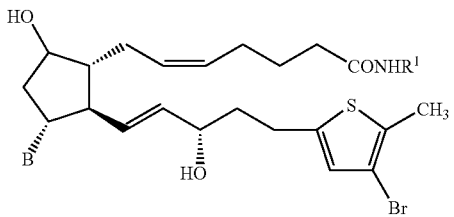

or a pharmaceutically acceptable salt or a prodrug thereof, wherein $R^1$ is H, ethyl, or hydroxyethyl.

Other compounds comprise one of the following

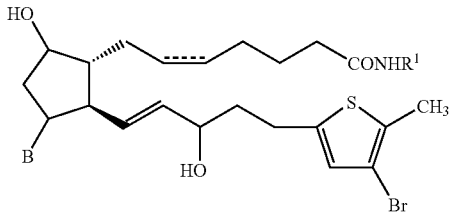

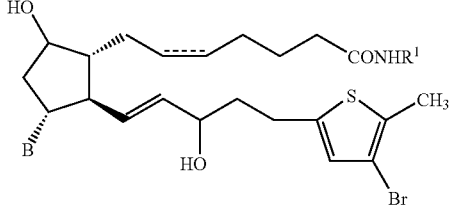

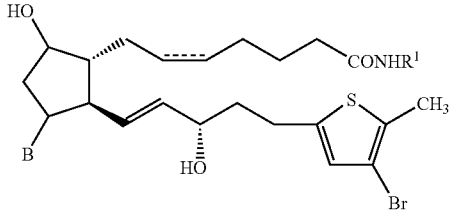

-continued

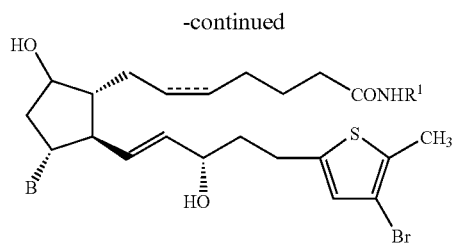

or a pharmaceutically acceptable salt or a prodrug thereof.

Other compounds comprise

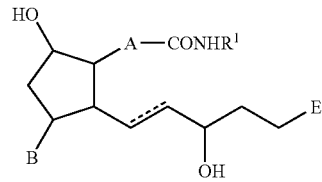

or a pharmaceutically acceptable salt or a prodrug thereof wherein $R^1$ is H, $C_{1-3}$ alkyl, or $C_{1-3}$ hydroxyalkyl; and E is an aromatic or a heteroaromatic moiety consisting of a single aromatic ring and one or two substituents, said ring consisting of five or six atoms, and said substituents being selected from the group consisting of bromo, chloro, flouro, methyl, and methoxy.

While not intending to limit the scope of the invention in any way, these compounds include the following or the like

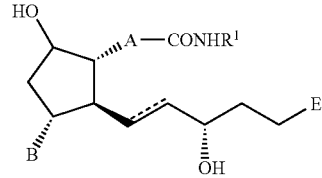

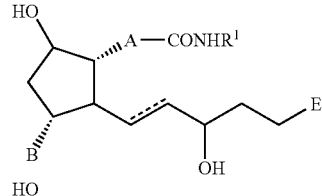

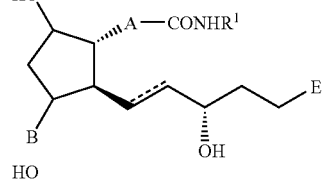

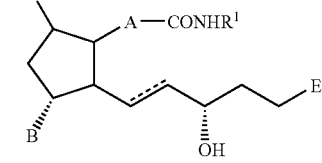

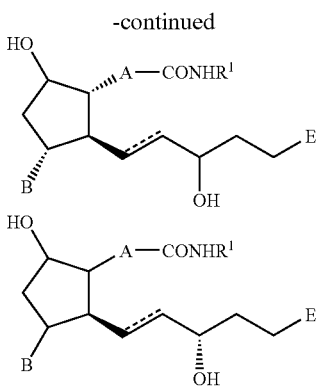

or a pharmaceutically acceptable salt or a prodrug thereof.
Other compounds comprise:

(Z)-7-{(1R,2R)-2-[(E)-(S)-5-(4-Bromo-5-methyl-thiophen-2-yl)-3-hydroxy-pent-1-enyl]-5-hydroxy-3-methyl-cyclopentyl}-hept-5-enoic acid (2-hydroxy-ethyl)-amide (scheme 2 16H,L, B=CH$_3$, R=CH$_2$CH$_2$OH);

(Z)-7-{(1R,2R)-2-[(E)-(S)-5-(4-Bromo-5-methyl-thiophen-2-yl)-3-hydroxy-pent-1-enyl]-5-hydroxy-3-methyl-cyclopentyl}-hept-5-enoic acid ethylamide (scheme 2 15H,L, B=CH$_3$, R=Et);

(Z)-7-{(1R,2R)-2-[(E)-(S)-5-(4-Bromo-5-methyl-thiophen-2-yl)-3-hydroxy-pent-1-enyl]-5-hydroxy-3-methyl-cyclopentyl}-hept-5-enoic acid amide (scheme 2 17H,L, B=CH$_3$, R=H);

(Z)-7-{(1R,2R)-2-[(E)-(S)-5-(4-Bromo-5-methyl-thiophen-2-yl)-3-hydroxy-pent-1-enyl]-3-ethyl-5-hydroxy-cyclopentyl}-hept-5-enoic acid (2-hydroxy-ethyl)-amide (scheme 2 18H, B=Et, R=CH$_2$CH$_2$OH);

(Z)-7-{(1R,2R)-2-[(E)-(S)-5-(4-Bromo-5-methyl-thiophen-2-yl)-3-hydroxy-pent-1-enyl]-3-ethyl-5-hydroxy-cyclopentyl}-hept-5-enoic acid ethylamide (scheme 2 19H, B=Et, R=Et);

(Z)-7-{(1R,2R)-2-[(E)-(S)-5-(4-Bromo-5-methyl-thiophen-2-yl)-3-hydroxy-pent-1-enyl]-3-ethyl-5-hydroxy-cyclopentyl}-hept-5-enoic acid amide (scheme 2 20, B=Et, R=H);

(Z)-7-{(1R,2S)-2-[(E)-(S)-5-(4-Bromo-5-methyl-thiophen-2-yl)-3-hydroxy-pent-1-enyl]-5-hydroxy-3-vinyl-cyclopentyl}-hept-5-enoic acid amide (scheme 2 13H,L, B=vinyl, R=H);

(Z)-7-{(1R,2S)-2-[(E)-(S)-5-(4-Bromo-5-methyl-thiophen-2-yl)-3-hydroxy-pent-1-enyl]-5-hydroxy-3-vinyl-cyclopentyl}-hept-5-enoic acid ethylamide (scheme 2 14H,L, B=vinyl, R=Et);

(Z)-7-{(1R,2S)-2-[(E)-(S)-5-(4-Bromo-5-methyl-thiophen-2-yl)-3-hydroxy-pent-1-enyl]-5-hydroxy-3-vinyl-cyclopentyl}-hept-5-enoic acid (2-hydroxy-ethyl)-amide (scheme 2 12H,L, B=vinyl, R=CH$_2$CH$_2$OH);

(Z)-7-{(1R,2R)-2-[(E)-(S)-5-(4-Bromo-5-methyl-thiophen-2-yl)-3-hydroxy-pent-1-enyl]-5-hydroxy-cyclopentyl}-hept-5-enoic acid amide (scheme 2 23H,L, B=H, R=H);

(Z)-7-{(1R,2R)-2-[(E)-(S)-5-(4-Bromo-5-methyl-thiophen-2-yl)-3-hydroxy-pent-1-enyl]-5-hydroxy-cyclopentyl}-hept-5-enoic acid ethylamide (scheme 2 21H,L, B=H, R=Et); or (Z)-7-{(1R,2R)-2-[(E)-(S)-5-(4-Bromo-5-methyl-thiophen-2-yl)-3-hydroxy-pent-1-enyl]-5-hydroxy-cyclopentyl}-hept-5-enoic acid (2-hydroxy-ethyl)-amide (scheme 2 22H,L, B=H, R=CH$_2$CH$_2$OH).

A "pharmaceutically acceptable salt" is any salt that retains the activity of the parent compound and does not impart any additional deleterious or untoward effects on the subject to which it is administered and in the context in which it is administered compared to the parent compound.

Pharmaceutically acceptable salts of acidic functional groups may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group.

The compounds of disclosed herein are useful for the prevention or treatment of glaucoma or ocular hypertension in mammals, or for the manufacture of a medicament for the treatment of glaucoma or ocular hypertension. These compounds may also be useful for the prevention or treatment of other diseases or conditions.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

EXAMPLE 1

Compound 1 was prepared by methods disclosed in U.S. Pat. No. 6,124,344, incorporated by reference herein.

(Z)-7-[(1R,2R,3R,5S)-2-[(E)-(S)-5-(4-Bromo-5-methyl-thiophen-2-yl)-3-(tetrahydro-pyran-2-yloxy)-pent-1-enyl]-3,5-bis-(tetrahydro-pyran-2-yloxy)-cyclopentyl]-hept-5-enoic acid methyl ester (2). An acetone (24 mL) solution of acid 1 was treated with DBU (1.4 mL, 9.36 mmol) and methyl iodide (0.6 mL, 9.63 mmol). The reaction was stirred for 21 h and then 50 mL 1 M HCl was added and the mixture extracted with ethyl acetate (3×50 mL). The combined ethyl acetate solution was dried ($Na_2SO_4$), filtered and evaporated to leave a brown oil that was used directly in the next step.

(Z)-7-{(1R,2R,3R,5S)-2-[(E)-(S)-5-(4-Bromo-5-methyl-thiophen-2-yl)-3-hydroxy-pent-1-enyl]-3,5-dihydroxy-cyclopentyl}-hept-5-enoic acid methyl ester (3). A mixture of the crude ester (2) in methanol (16 mL) was treated with pyridinium p-toluenesulfonate (2.625 g, 10.4 mmol). After 21 h, the solvent was evaporated in vacuo and the residue purified by flash chromatography on silica gel (90% ethyl acetate/hexanes→95%) to give 3 (3.453 g, 6.9 mmol, 86% for the two steps).

(Z)-7-[(1R,2R,3R,5S)-2-[(E)-(S)-5-(4-Bromo-5-methyl-thiophen-2-yl)-3-(tert-butyl-dimethyl-silanyloxy)-pent-1-enyl]-3-(tert-butyl-dimethyl-silanyloxy)-5-hydroxy-cyclopentyl]-hept-5-enoic acid methyl ester (4). A dichloromethane (14 mL) solution of 3 (3.452 g, 6.9 mmol) was treated with triethylamine (2.9 mL, 20.8 mmol), DMAP (211 mg, 1.73 mmol) and TBSCl (2.130 g, 14.1 mmol). The reaction was allowed to stir for 22 h and then was quenched by addition of 100 mL saturated $NaHCO_3$ solution. The mixture was extracted with $CH_2Cl_2$ (3×75 mL) and the combined $CH_2Cl_2$ solution was dried ($Na_2SO_4$), filtered and evaporated. Purification by flash chromatography (10% ethyl acetate/hexane→20%) gave 4 (3.591 g, 4.9 mmol, 71%).

(Z)-7-[(1R,2R,3R)-2-[(E)-(S)-5-(4-Bromo-5-methyl-thiophen-2-yl)-3-(tert-butyl-dimethyl-silanyloxy)-pent-1- enyl]-3-(tert-butyl-dimethyl-silanyloxy)-5-oxo-cyclopentyl]-hept-5-enoic acid methyl ester (5). A mixture of alcohol 4 (3.591 g, 4.9 mmol), 4A molecular sieves (2.5 g), and NMO (867 mg, 7.4 mmol) in dichloromethane (10 mL) was treated with TPAP (117 mg, 0.33 mmol). After 1 h, the mixture was filtered through celite and the filtrate evaporated in vacuo. Purification by flash chromatography (5% ethyl acetate/hexanes→7.5%) gave 5 (2.984 g, 4.1 mmol, 84%).

(Z)-7-{(1R,2S)-2-[(E)-(S)-5-(4-Bromo-5-methyl-thiophen-2-yl)-3-hydroxy-pent-1-enyl]-5-oxo-cyclopent-3-enyl}-hept-5-enoic acid methyl ester (6). A mixture of 5 (1.486 g, 2.03 mmol), HOAc (20 mL), $H_2O$ (10 mL) and THF (10 mL) was stirred at 70° C. for 17 h. The reaction was then poured into 750 mL saturated $NaHCO_3$ solution and the resulting mixture was extracted with ethyl acetate (4×200 mL). The combined ethyl acetate solution was dried ($Na_2SO_4$), filtered and evaporated. Flash chromatography (50% ethyl acetate/hexanes) gave 6 (497 mg, 1.03 mmol, 51%).

(Z)-7-{(1R,2S)-2-[(E)-(S)-5-(4-Bromo-5-methyl-thiophen-2-yl)-3-(tert-butyl-dimethyl-silanyloxy)-pent-1-enyl]-5-oxo-cyclopent-3-enyl}-hept-5-enoic acid methyl ester (7). A dichloromethane (6 mL) solution of 6 (497 mg, 1.03 mmol) was treated with 2,6-lutidine (143 μL, 1.22 mmol) and TBSOTf (0.26 mL, 1.13 mmol). After 1.5 h, 50 mL saturated $NaHCO_3$ was added and the resulting mixture was extracted with 25 mL $CH_2Cl_2$. The $CH_2Cl_2$ layer was washed with 50 mL 1 M HCl and 50 mL brine. The $CH_2Cl_2$ solution was then dried ($Na_2SO_4$), filtered and evaporated. Purification by flash chromatography (8% ethyl acetate/hexanes→10%) gave 7 (553 mg, 0.93 mmol, 90%).

(Z)-7-{(1R,2S)-2-[(E)-(S)-5-(4-Bromo-5-methyl-thiophen-2-yl)-3-(tert-butyl-dimethyl-silanyloxy)-pent-1-enyl]-5-oxo-3-vinyl-cyclopentyl}-hept-5-enoic acid methyl ester (8, B=vinyl). Vinylmagnesium bromide (1.25 mL, 1.25 mmol, 1 M/THF) was added to a 0° C. mixture of CuI (158 mg, 0.83 mmol) in 2 mL THF. The dark mixture was stirred for 5 min. and then was cooled to −78° C. A solution of Enone 7 (169 mg, 0.28 mmol) in 1 mL THF was added by cannula, rinsing with 0.25 mL THF. The mixture was stirred for 1.5 h and then 20 mL saturated $NH_4Cl$ was added. The resulting mixture was stirred for 20 min. and then was extracted with ethyl acetate (3×20 mL). The combined ethyl acetate solution was dried ($Na_2SO_4$), filtered and evaporated. Purification by flash chromatography on silica gel (7.5% ethyl acetate/hexanes) gave the title ketone (138 mg, 0.22 mmol, 79%).

(Z)-7-{(1R,2R)-2-[(E)-(S)-5-(4-Bromo-5-methyl-thiophen-2-yl)-3-(tert-butyl-dimethyl-silanyloxy)-pent-1-enyl]-5-oxo-cyclopentyl}-hept-5-enoic acid methyl ester (8, B=H). A solution of 7 (170 mg, 0.28 mmol) in 4 mL toluene was added, by cannula, to a −40° C. mixture of hydrido(triphenylphosphine)copper(I) hexamer (300 mg, 0.15 mmol) in 4 mL toluene, rinsing with 0.5 mL toluene. The temperature was allowed to warm to 0° C. over 1 h and then was allowed to warm to room temperature. After a further 1 h, the reaction was quenched by addition of 15 mL saturated $NH_4Cl$ solution. The mixture was extracted with ethyl acetate (3×15 mL) and the combined ethyl acetate solution dried ($Na_2SO_4$), filtered and evaporated. Purification by flash chromatography (8% ethyl acetate/hexanes to 10%) gave the title ketone (150 mg, 0.25 mmol, 89%).

(Z)-7-{(1R,2R)-2-[(E)-(S)-5-(4-Bromo-5-methyl-thiophen-2-yl)-3-(tert-butyl-dimethyl-silanyloxy)-pent-1-enyl]-3-methyl-5-oxo-cyclopentyl}-hept-5-enoic acid methyl ester Ketone 8 (B=$CH_3$). A −78° C. mixture of CuCN (121 mg, 1.35 mmol) in THF (1 mL) was treated with MeLi (1.4 mL, 1.96 mmol, 1.4 M/ether). The mixture was stirred for 5 min. at −78° C. and for 10 min. at room temperature. The resulting solution was recooled to −78° C. and a solution of enone 7 (211 mg, 0.35 mmol) in THF (1 mL) was added by cannula, rinsing with 0.5 mL THF. After 45 min., 25 mL saturated $NH_4Cl$ solution was added and the mixture stirred for 15 min. The mixture was extracted with dichloromethane (3×20 mL) and the combined dichloromethane solution dried ($Na_2SO_4$), filtered and evaporated to give 175 mg of 8.

(Z)-7-{(1R,2R)-2-[(E)-(S)-5-(4-Bromo-5-methyl-thiophen-2-yl)-3-(tert-butyl-dimethyl-silanyloxy)-pent-1-enyl]-5-hydroxy-3-methyl-cyclopentyl}-hept-5-enoic acid methyl ester Alcohols 9 (B=$CH_3$). A methanol (0.8 mL) solution of ketone 8 (B=$CH_3$, 102 mg, 0.17 mmol) was treated with $NaBH_4$ (11 mg, 0.29 mmol). After 1.5 h, the reaction was quenched with 15 mL 1 M HCl and the resulting mixture extracted with dichloromethane (3×15 mL). The combined dichloromethane solution was washed with brine (25 mL) and then was dried ($Na_2SO_4$), filtered and evaporated to give 98 mg of the alcohols 9.

(Z)-7-{(1R,2R)-2-[(E)-(S)-5-(4-Bromo-5-methyl-thiophen-2-yl)-3-hydroxy-pent-1-enyl]-5-hydroxy-3-methyl-cyclopentyl}-hept-5-enoic acid methyl ester Diols 10 (B=$CH_3$). A solution of alcohols 9 (B=$CH_3$, 117 mg, 0.19 mmol) in HOAc (1.6 mL)/$H_2O$ (0.8 mL)/THF (0.8 mL) was heated at 70° C. for 2 h and then stored in the freezer overnight. The reaction was incomplete and so was heated at 70° C. for a further 2 h. The reaction was quenched by addition of 100 mL saturated $NaHCO_3$ solution and the resulting mixture was extracted with ethyl acetate (4×100 mL). The combined ethyl acetate solution was dried ($Na_2SO_4$), filtered and evaporated. Flash chromatography (30% ethyl acetate/hexanes to 35% to 40% o 50%) gave two C9 diastereomers: high Rf 35 mg (0.07 mmol, 32%) and low Rf 46 mg (0.092 mmol, 42%).

(Z)-7-{(1R,2R)-2-[(E)-(S)-5-(4-Bromo-5-methyl-thiophen-2-yl)-3-hydroxy-pent-1-enyl]-5-hydroxy-3-methyl-cyclopentyl}-hept-5-enoic acid Acid 11 (high Rf diastereomer). A THF (1.6 mL) solution of 10 (B=$CH_3$, 35 mg, 0.07 mmol) was treated with 0.5 M LiOH (0.42 mL, 0.21 mmol). The reaction was allowed to stir for 24 h and then 10 mL 1 M HCl was added. The resulting mixture was extracted with dichloromethane (3×15 mL) and the combined dichloromethane solution was dried ($Na_2SO_4$), filtered and evaporated. Purification by flash chromatography (5% methanol/dichloromethane→7%) gave the title acid (30 mg, 0.06 mmol, 88%).

(Z)-7-{(1R,2R)-2-[(E)-(S)-5-(4-Bromo-5-methyl-thiophen-2-yl)-3-hydroxy-pent-1-enyl]-5-hydroxy-3-methyl-cyclopentyl}-hept-5-enoic acid ethylamide Amide 15 (B=$CH_3$, R=ethyl). A solution of acid 11 (B=$CH_3$, 5.2 mg, 0.011 mmol) in dichloromethane (0.2 mL) was treated with triethylamine (2 μL, 0.014 mmol) and ethyl chloroformate (2

μL, 0.021 mmol). After 1 h, ethylamine (10 mL, 0.020 mmol, 2 M/THF) was added. The solution was allowed to stir for 19 h and then 10 mL 1 M HCl was added. The mixture was extracted with dichloromethane (2×15 mL) and the combined dichloromethane solution was washed with 10 mL saturated $NaHCO_3$ solution and 10 mL brine. The solution was then dried ($Na_2SO_4$), filtered and evaporated. Purification by preparative thin layer chromatography (4% methanol/dichloromethane) gave the title amide (7 mg, 0.01 mmol, 100%). 300 MHz NMR ($CDCl_3$, ppm) d 6.58 (1H, s) 5.5–5.4 (4 H, m) 4.4–4.1 (1 H, m) 4.0–3.9 (1 H, m) 3.3–3.2 (2 H, m) 2.9–2.8 (2 H, m) 2.32 (3 H, s) 2.3–1.5 (17 H, m) 1.12 (3 H, t, J=7.3 Hz) 0.91 (3 H, d, J=6.6 Hz). The other secondary amides were prepared in an analogous fashion.

(Z)-7-{(1R,2R)-2-[(E)-(S)-5-(4-Bromo-5-methyl-thiophen-2-yl)-3-hydroxy-pent-1-enyl]-5-hydroxy-3-methyl-cyclopentyl}-hept-5-enoic acid amide 17 (B=$CH_3$, R=H). The primary amides were prepared similarly to the secondary amides with concentrated $NH_4OH$ (aq) being used as the nitrogen source in large excess (10–20 equivalents).

EXAMPLE 2

The biological activity of the compounds shown below, prepared as described in Example 1 was tested using the following procedures.

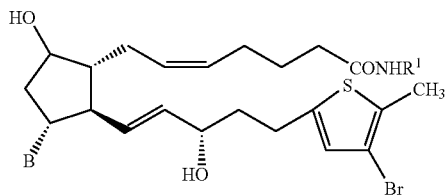

| Compound | B | R | Diastereomer |
|---|---|---|---|
| 12H | vinyl | —$CH_2CH_2OH$ | High Rf |
| 12L | vinyl | —$CH_2CH_2OH$ | Low Rf |
| 13L | vinyl | H | Low Rf |
| 13H | vinyl | H | High Rf |
| 14L | vinyl | ethyl | Low Rf |
| 14H | vinyl | ethyl | High Rf |
| 15H | methyl | ethyl | High Rf |
| 15L | methyl | ethyl | Low Rf |
| 16L | methyl | —$CH_2CH_2OH$ | Low Rf |
| 16H | methyl | —$CH_2CH_2OH$ | High Rf |
| 17L | methyl | H | Low Rf |
| 17H | methyl | H | High Rf |
| 18H | ethyl | —$CH_2CH_2OH$ | High Rf |
| 19H | ethyl | ethyl | High Rf |
| 20H | ethyl | H | High Rf |
| 21H | H | ethyl | High Rf |
| 21L | H | ethyl | Low Rf |
| 22H | H | —$CH_2CH_2OH$ | High Rf |
| 22L | H | —$CH_2CH_2OH$ | Low Rf |
| 23H | H | H | High Rf |
| 23L | H | H | High Rf |

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), were cultured in 100 mm culture dishes in high-glucose DMEM medium containing 10% fetal bovine serum, 2 mM 1-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells were seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates were washed four times with HBSS-HEPES buffer to remove excess dye leaving 100 μl in each well. Plates were re-equilibrated to 37° C. for a few minutes.

Cells were excited with an Argon laser at 488 nm, and emission was measured through a 510–570 nm bandwidth emission filter (FLIPR™, Molecular Devices, Sunnyvale, Calif.). Drug solution was added in a 50 μl volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2$ ($hEP_1$; $hEP_2$/Gqs5; $hEP_{3A}$/Gqi5; $hEP_4$/Gqs5); $PGF_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an $n \geq 3$.

feFP OHL Assay

Functional FP-receptor studies were performed using iris sphincter muscles from cat eyes. The eyes were either used directly after enucleation or stored in ice cold saline overnight. The iris sphincter muscles were prepared, cut in halves, and mounted in thermostated (37° C.) tissue baths with oxygenated modified Kreb's solution containing indomethacin ($2.8 \times 10^{-6}$ M), atropine ($10^{-7}$ M) and propranolol ($10^{-7}$ M). A resting tension of 150 mg was applied, and the contractile force was measured isometrically after cumulative dosing of test compounds. A manual or automated tissue bath system (Buxco, STC 400) was used for the experiments. For each tissue sample the maximal response was normalized to 100%. The mean response of two to four different preparations was calculated.

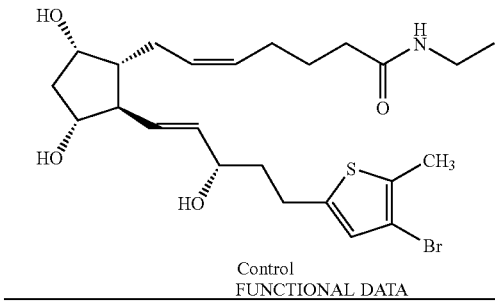

Control

FUNCTIONAL DATA

| Compound | HFP | HEP1 | HEP2 | HEP3A | HEP4 | HTP | HIP | HDP | feFP OHL |
|---|---|---|---|---|---|---|---|---|---|
| Control | 2138 | NA | NA | NA | NA | NA | NA | NA | 25 |
| 15L | NA | NA | NA | NA | >10,000 | NA | NA | NA | >10,000 |
| 15H | >10,000 | NA | NA | NA | >10,000 | >10,000 | NA | NA | 89 |
| 16L | NA | NA | NA | NA | >10,000 | NA | NA | NA | NA |
| 16H | 10000 | NA | NA | NA | >10,000 | 1381 | NA | NA | 33 |
| 17L | >10,000 | NA | NA | NA | NA | NA | NA | NA | |
| 17H | 10000 | NA | NA | NA | >10,000 | 1950 | NA | NA | |
| 13L | NA | NA | NA | NA | >10,000 | NA | NA | NA | |
| 13H | 584 | NA | NA | 7080 | >10,000 | 2523 | >10,000 | NA | |
| 14L | NA | NA | NA | NA | NA | NA | NA | NA | NA |
| 14H | >10,000 | NA | NA | NA | NA | NA | NA | NA | 86 |
| 12H | >10,000 | NA | NA | NA | >10,000 | >10,000 | >10,000 | NA | 182 |
| 12L | >10,000 | NA | NA | 10000 | NA | >10,000 | >10,000 | NA | >10,000 |
| 18H | NA | NA | NA | NA | NA | NA | NA | NA | 906 |
| 19H | NA | NA | NA | NA | NA | NA | NA | NA | 687 |
| 20H | 5422 | NA | NA | >10⁵ | NA | >10⁵ | NA | | 766 |
| 21H | >10,000 | NA | NA | NA | NA | >10,000 | NA | NA | 71 |
| 21L | NA | NA | NA | NA | NA | NA | NA | NA | >10⁵ |
| 22H | >10,000 | NA | NA | NA | NA | >10,000 | NA | NA | 155 |
| 22L | NA | NA | NA | NA | NA | NA | NA | NA | 1170 |
| 23H | >10,000 | NA | NA | NA | NA | 2126 | NA | NA | 163 |
| 23L | NA | NA | NA | NA | NA | NA | NA | NA | 5130 |

The results of the binding and activity studies presented in the table demonstrate that the compounds disclosed herein are selective agonists in the feFP OHL functional assay, and are thus useful for the treatment of glaucoma, ocular hypertension, the other diseases or conditions disclosed herein.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound of the formula

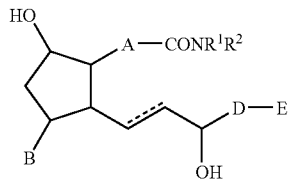

or a pharmaceutically acceptable salt or a prodrug thereof, wherein a dashed line represents the presence or absence of a bond;

A is $-(CH_2)_6-$, or cis-$CH_2-CH=CH-(CH_2)_3-$, wherein 1 or 2 carbons may be replaced by S or O;

B is hydrogen, a $C_{1-6}$ hydrocarbon, or $-(CH_2)_m X(CH_2)_p H$, wherein m is at least 1 and the sum of m and p is from 1 to 5;

$R^1$ and $R^2$ are independently H, $C_{1-6}$ alkyl, or $C_{1-6}$ hydroxyalkyl;

D is $-(CH_2)_n-$, $-CH_2X(CH_2)_n-$, or $-(CH_2)_n X-$, wherein n is from 0 to 4;

X is S or O; and

E is substituted or unsubstituted thienyl.

2. The compound of claim 1 of the formula

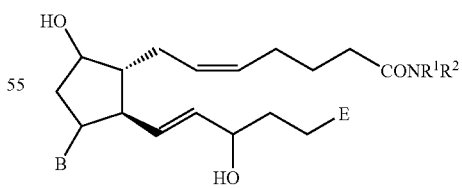

or a pharmaceutically acceptable salt or a prodrug thereof.

3. The compound of claim 2 wherein E is thienyl having from 1 to 3 substituents, wherein said substituents are selected from the group consisting of methyl, methoxy, bromo, chloro, and fluoro.

4. The compound of claim 2 wherein E is thienyl having from 2 to 4 substituents.

5. The compound of claim 1 wherein A is —(CH$_2$)$_6$— or cis-CH$_2$CH=CH—(CH$_2$)$_3$— having no heteroatom substitution.

6. The compound of claim 1 wherein E is thienyl having one methyl and one bromo substituent.

7. The compound of claim 3 of the formula

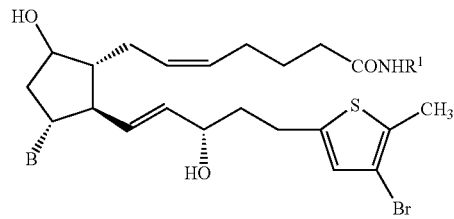

or a pharmaceutically acceptable salt or a prodrug thereof, wherein R$^1$ is H, ethyl, or hydroxyethyl.

8. The compound of claim 1 wherein B is hydrogen.
9. The compound of claim 1 wherein B is methyl.
10. The compound of claim 1 wherein B is ethyl.
11. The compound of claim 1 wherein B is vinyl.
12. The compound of claim 1 wherein R$^1$ and R$^2$ are H.
13. The compound of claim 1 wherein R$^1$ is H and R$^2$ is ethyl.
14. The compound of claim 1 wherein R$^1$ is H and R$^2$ is hydroxyethyl.
15. The compound of claim 7 selected from the group consisting of (Z)-7-{(1R,2R)-2-[(E)-(S)-5-(4-Bromo-5-methyl-thiophen-2-yl)-3-hydroxy-pent-1-enyl]-5-hydroxy-3-methyl-cyclopentyl}-hept-5-enoic acid (2-hydroxy-ethyl)-amide;

(Z)-7-{(1R,2R)-2-[(E)-(S)-5-(4-Bromo-5-methyl-thiophen-2-yl)-3-hydroxy-pent-1-enyl]-5-hydroxy-3-methyl-cyclopentyl}-hept-5-enoic acid ethylamide;

(Z)-7-{(1R,2R)-2-[(E)-(S)-5-(4-Bromo-5-methyl-thiophen-2-yl)-3-hydroxy-pent-1-enyl]-5-hydroxy-3-methyl-cyclopentyl}-hept-5-enoic acid amide;

(Z)-7-{(1R,2R)-2-[(E)-(S)-5-(4-Bromo-5-methyl-thiophen-2-yl)-3-hydroxy-pent-1-enyl]-3-ethyl-5-hydroxy-cyclopentyl}-hept-5-enoic acid (2-hydroxy-ethyl)-amide;

(Z)-7-{(1R,2R)-2-[(E)-(S)-5-(4-Bromo-5-methyl-thiophen-2-yl)-3-hydroxy-pent-1-enyl]-3-ethyl-5-hydroxy-cyclopentyl}-hept-5-enoic acid ethylamide;

(Z)-7-{(1R,2R)-2-[(E)-(S)-5-(4-Bromo-5-methyl-thiophen-2-yl)-3-hydroxy-pent-1-enyl]-3-ethyl-5-hydroxy-cyclopentyl}-hept-5-enoic acid amide;

(Z)-7-{(1R,2S)-2-[(E)-(S)-5-(4-Bromo-5-methyl-thiophen-2-yl)-3-hydroxy-pent-1-enyl]-5-hydroxy-3-vinyl-cyclopentyl}-hept-5-enoic acid amide;

(Z)-7-{(1R,2S)-2-[(E)-(S)-5-(4-Bromo-5-methyl-thiophen-2-yl)-3-hydroxy-pent-1-enyl]-5-hydroxy-3-vinyl-cyclopentyl}-hept-5-enoic acid ethylamide;

(Z)-7-{(1R,2S)-2-[(E)-(S)-5-(4-Bromo-5-methyl-thiophen-2-yl)-3-hydroxy-pent-1-enyl]-5-hydroxy-3-vinyl-cyclopentyl}-hept-5-enoic acid (2-hydroxy-ethyl)-amide;

(Z)-7-{(1R,2R)-2-[(E)-(S)-5-(4-Bromo-5-methyl-thiophen-2-yl)-3-hydroxy-pent-1-enyl]-5-hydroxy-cyclopentyl}-hept-5-enoic acid amide;

(Z)-7-{(1R,2R)-2-[(E)-(S)-5-(4-Bromo-5-methyl-thiophen-2-yl)-3-hydroxy-pent-1-enyl]-5-hydroxy-cyclopentyl}-hept-5-enoic acid ethylamide; and (Z)-7-{(1R,2R)-2-[(E)-(S)-5-(4-Bromo-5-methyl-thiophen-2-yl)-3-hydroxy-pent-1-enyl]-5-hydroxy-cyclopentyl}-hept-5-enoic acid (2-hydroxy-ethyl)-amide.

16. A method of treating glaucoma or ocular hypertension comprising administering to a mammal an effective amount the compound of claim 1 of

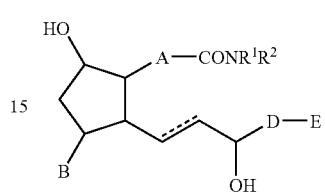

or a pharmaceutically acceptable salt or a prodrug thereof.

17. The method of claim 16 wherein A is cis-CH$_2$CH=CH—(CH$_2$)$_3$—.

18. The method of claim 16 wherein E is disubstituted thienyl.

19. The method of claim 16 wherein the compound has the formula

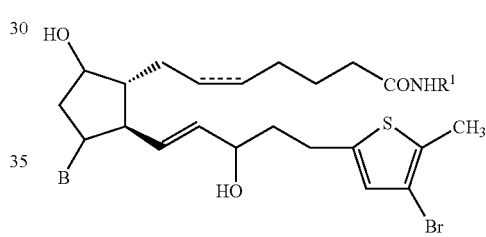

or a pharmaceutically acceptable salt or a prodrug thereof.

20. The method of claim 16 comprising

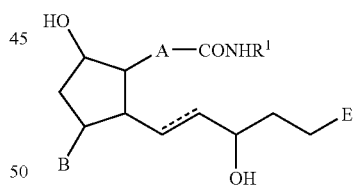

or a pharmaceutically acceptable salt or a prodrug thereof, wherein

R$^1$ is H, C$_{1-3}$ alkyl, or C$_{1-3}$ hydroxyalkyl; and

E is a substituted thienyl having one or two substituents selected from the group consisting of bromo, chloro, flouro, methyl, and methoxy.

21. The compound of claim 1 wherein E is thienyl having substituents comprising from 1 to 6 non-hydrogen atoms each.

* * * * *